(12) United States Patent
Kumagai et al.

(10) Patent No.: US 7,432,335 B2
(45) Date of Patent: Oct. 7, 2008

(54) BASIC SILANE COUPLING AGENT ORGANIC CARBOXYLATE COMPOSITION, METHOD FOR PRODUCING THE SAME, AND EPOXY RESIN COMPOSITION CONTAINING THE SAME

(75) Inventors: Masashi Kumagai, Hitachi (JP); Takashi Ouchi, Kitaibaraki (JP); Katsuyuki Tsuchida, Kitaibaraki (JP)

(73) Assignee: Nikko Materials Co., Ltd., Tokyo (JP)

( * ) Notice: Subject to any disclaimer, the term of this patent is extended or adjusted under 35 U.S.C. 154(b) by 341 days.

(21) Appl. No.: 11/444,728

(22) Filed: Jun. 1, 2006

(65) Prior Publication Data

US 2006/0217494 A1  Sep. 28, 2006

Related U.S. Application Data

(62) Division of application No. 10/450,421, filed as application No. PCT/JP02/08620 on Aug. 27, 2002, now Pat. No. 7,094,845.

(30) Foreign Application Priority Data

Dec. 7, 2001  (JP) .............................. 2001-374408
May 21, 2002  (JP) .............................. 2002-146196

(51) Int. Cl.
*C08L 61/06* (2006.01)
*C08L 63/02* (2006.01)

(52) U.S. Cl. .................... 525/504; 252/182.28; 525/56; 525/109; 525/113; 525/423; 525/431; 525/453; 525/454; 525/476; 525/477; 525/533

(58) Field of Classification Search ........................ None
See application file for complete search history.

(56) References Cited

U.S. PATENT DOCUMENTS 3,773,607 A  11/1973  Marzocchi
5,627,227 A  5/1997  Suga et al.
5,679,798 A  10/1997  Berger et al.
6,140,414 A  10/2000  Ohsawa et al.
6,710,181 B2  3/2004  Kumagai et al.

FOREIGN PATENT DOCUMENTS

| JP | 5-186479 | 7/1993 |
|---|---|---|
| JP | 6-279458 | 10/1994 |
| JP | 6-279463 | 10/1994 |
| JP | 9-12683 | 1/1997 |
| JP | 09-180542 | 7/1997 |
| JP | 9-295988 | 11/1997 |
| JP | 9-295989 | 11/1997 |
| JP | 9-295990 | 11/1997 |
| JP | 9-295991 | 11/1997 |
| JP | 9-296135 | 11/1997 |
| JP | 09-310043 | 12/1997 |
| JP | 10-273492 | 10/1998 |
| JP | 2000-063747 | 2/2000 |
| JP | 2000-297094 | 10/2000 |
| JP | 2001-187836 | 7/2001 |
| JP | 2001-348393 | 12/2001 |
| WO | WO 01/77119 | 10/2001 |

OTHER PUBLICATIONS

Detroit Society for Paint Technology, "Powder Coating: Why-How-When," vol. 44, No. 565, Feb. 1972, pp. 30-37.

*Primary Examiner*—Robert Sellers
(74) *Attorney, Agent, or Firm*—Flynn, Thiel, Boutell & Tanis, P.C.

(57) ABSTRACT

There are provided a composition for functioning as an effective additive for epoxy resin that is solid at room temperature and has high storage stability, and a method thereof. The composition of the present invention is a basic silane coupling agent organic carboxylate composition obtained by first synthesizing an organic carboxylate of a basic silane coupling agent by reacting a basic silane coupling agent and an organic carboxylic acid, and subsequently heating and mixing the organic carboxylate of the basic silane coupling agent with a compound exhibiting good affinity for the basic silane coupling agent or organic carboxylic acid and having a softening point or melting point of 40° C. or greater.

2 Claims, No Drawings

BASIC SILANE COUPLING AGENT ORGANIC CARBOXYLATE COMPOSITION, METHOD FOR PRODUCING THE SAME, AND EPOXY RESIN COMPOSITION CONTAINING THE SAME

This is a division of Ser. No. 10/450,421, filed Jun. 12, 2003, now U.S. Pat. No. 7,094,845 which was the national stage of International Application No. PCT/JP02/08620, filed Aug. 27, 2002, which International Application was not published in English.

TECHNICAL FIELD

The present invention relates to a new composition made up of an organic carboxylate of a basic silane coupling agent and a compound exhibiting a good affinity for the basic silane coupling agent or organic carboxylic acid and having a softening point or melting point of 40° C. or greater, the new composition being capable of exhibiting exceptional storage stability and enhanced adhesion as an additive for powdered paints and one-component epoxy resin compositions or as an additive for sealing resins, and to a producing method and utilization thereof.

BACKGROUND ART

Imidazoles are curing agents that are receiving attention for providing exceptional curing properties to resin compositions, resulting in cured materials with a high heat resistance. However, because of problems with storage stability, extending their working life by controlling basicity is being investigated through formation of metal complexes and various types of acid salts. The inventors have filed patent applications (Japanese Patent Application Publication Nos. 9-12683 and 2000-297094) in which at least one of imidazole group-containing silane coupling agents expressed by the general formulas (1) through (4) below would provide, as curing agents for epoxy resins, a curing epoxy resin composition having exceptional adhesion properties. However, these imidazole group-containing silane coupling agents are disadvantageous in having a poor storage stability when mixed with an epoxy resin in the same manner as in the case of conventional imidazoles.

Poor storage stability when mixed with an epoxy resin is also a problem with silane coupling agents such as amino group-containing silane coupling agents (commercial products), dialkylamino group-containing silane coupling agents (Japanese Patent Application Publication Nos. 9-295988, 9-296135, and 9-295989), monomethylamino group-containing silane coupling agents (commercial products), benzimidazole group-containing silane coupling agents (Japanese Patent Application Publication No. 6-279458), benzotriazole group-containing silane coupling agents (Japanese Patent Application Publication No. 6-279463), or pyridine ring-containing silane coupling agents (Japanese Patent Application Publication Nos. 9-295990 and 9-295991).

DISCLOSURE OF THE INVENTION

The present invention provides a composition that is a solid at room temperature and that provides a stable, long working life without compromising the desirable adhesion characteristics of the above-mentioned silane coupling agents, yet melts at a prescribed temperature and has a silane coupling functionality capable of contributing to the curing reaction, and a method for producing the same; and is aimed at application to an epoxy resin thereof.

As a result of extensive investigation, the inventors discovered that a basic silane coupling agent organic carboxylate composition obtained by a specific method not only had exceptional storage stability as an additive for an epoxy resin, but also yielded a significant enhancement to its adhesion properties. The present invention is based upon this discovery, and comprises [1] through [6] below.

[1] A basic silane coupling agent organic carboxylate composition, obtained by a process in which an organic carboxylate of a basic silane coupling agent obtained by reacting a basic silane coupling agent and an organic carboxylic acid is heated and mixed with a compound exhibiting good affinity for the basic silane coupling agent or organic carboxylic acid and having a softening point or melting point of 40° C. or greater.

[2] A method for producing the basic silane coupling agent organic carboxylate composition according to [1], the method comprising:

producing an organic carboxylate of a basic silane coupling agent by reacting a basic silane coupling agent and an organic carboxylic acid; and subsequently heating and mixing the organic carboxylate of the basic silane coupling agent and a compound exhibiting good affinity for the basic silane coupling agent or organic carboxylic acid and having a softening point or melting point of 40° C. or greater.

[3] The basic silane coupling agent organic carboxylate composition according to [1], wherein the basic silane coupling agent is comprised of at least one selected from the group consisting of the compounds expressed by the general formulas (1) through (4) below, or at least one of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents.

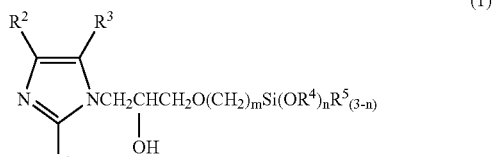

(1)

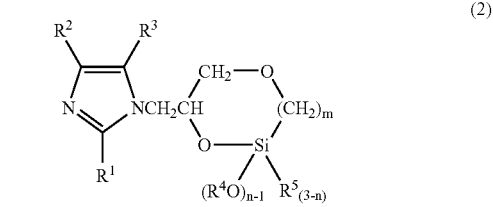

(2)

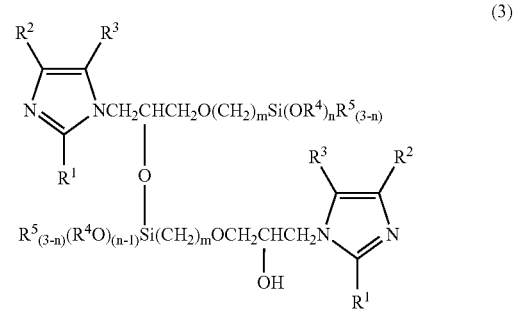

(3)

-continued

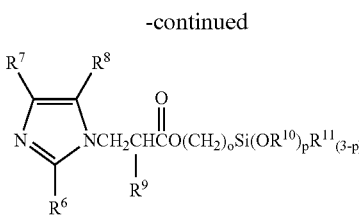

(4)

wherein in the general formulas (1) through (4), $R^1$ to $R^3$ each represent hydrogen, a vinyl group, or an alkyl group having 1 to 20 carbon atoms wherein the $R^2$ and $R^3$ may form an aromatic ring;

$R^4$ and $R^5$ each represent an alkyl group having 1-5 carbon atoms;

$R^6$ to $R^8$ each represent hydrogen, an alkyl group having 1 to 20 carbon atoms, a vinyl group, a phenyl group, or a benzyl group wherein $R^7$ and $R^8$ may bond and form an aromatic ring;

$R^9$ represents hydrogen or an alkyl group having 1 to 3 carbon atoms;

$R^{10}$ and $R^{11}$ each represent an alkyl group having 1 to 5 carbon atoms; and m, n, o, and p are integers of 1 to 10, 1 to 3, 1 to 10, and 1 to 3, respectively.

[4] The method for producing a basic silane coupling agent organic carboxylate composition according to [2], wherein the basic silane coupling agent is comprised of at least one selected from the group consisting of the compounds expressed by the general formulas (1) through (4), or at least one selected from the group consisting of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents.

[5] An additive for an epoxy resin containing the basic silane coupling agent organic carboxylate composition according to [1] or [3].

[6] An epoxy resin composition containing the basic silane coupling agent organic carboxylate composition according to [1] or [3].

The present invention will be described in further detail hereafter.

In the imidazole group-containing silane coupling agents for which the basic silane coupling agents are expressed by the general formulas (1), (2), and (3) above, $R^1$ to $R^3$ each represent hydrogen, a vinyl group, or an alkyl group having 1 to 20 carbon atoms, and aromatic rings may be formed from $R^2$ and $R^3$. $R^4$ and $R^5$ each represent an alkyl group having 1 to 5 carbon atoms, and m and n represent integers of 1 to 10 and 1 to 3, respectively. Within this range, a value of 3 is particularly preferable for m. In the general formula (4) above, $R^6$ to $R^8$ each represent hydrogen, an alkyl group having 1 to 20 carbon atoms, a vinyl, a phenyl group, or a benzyl group; $R^9$ represents hydrogen or an alkyl group having 1 to 3 carbon atoms, and $R^{10}$ and $R^{11}$ each represent an alkyl group having 1 to 5 carbon atoms. Furthermore, o and p are integers of 1 to 10 and 1 to 3, respectively. Also, $R^7$ and $R^8$ may bond and form an aromatic ring.

The compounds expressed by the general formulas (1) through (3) above can be synthesized based on the method disclosed in Japanese Patent Application Publication No. 5-186479, and the compound expressed by the general formula (4) above can be synthesized based on the method disclosed in Japanese Patent Application Publication No. 2000-297094. The compounds of the general formulas (1) through (3) above are often obtained as a mixture of three types in the producing process, for which separation and purification procedures are not particularly necessary, and a mixture thereof is suitable for use as-is.

Amino group-containing silane coupling agents include (3-aminopropyl)trimethoxysilane, (3-aminopropyl)triethoxysilane, (3-aminopropyl)dimethoxymethylsilane, (3-aminopropyl)diethoxymethylsilane, N-(2-aminoethyl)-3-aminopropyltrimethoxysilane, and the like. Monomethylamino group-containing silane coupling agents include N-methylaminopropyltrimethoxysilane, N-methylaminopropyltriethoxysilane, and the like. Dialkylamino group-containing silane coupling agents include those disclosed in Japanese Patent Application Publication Nos. 9-295988, 9-296135, and 9-295989. Among these, dimethylamino group-containing silane coupling agents are particularly preferred. Benzotriazole-containing silane coupling agents include those disclosed in Japanese Patent Application Publication No. 6-279463, benzimidazole group-containing silane coupling agents include those disclosed in Japanese Patent Application Publication No. 6-279458, and pyridine ring-containing silane coupling agents include those disclosed in Japanese Patent Application Publication Nos. 9-295990 and 9-295991.

The basic silane coupling agent organic carboxylate composition of the present invention is obtained by reacting at least one selected from the above-mentioned basic silane coupling agents with an organic carboxylic acid at 50-200° C. and mixing the product at a heating temperature of 50-200° C. with a compound exhibiting a good affinity for the basic silane coupling agent or organic carboxylic acid and having a softening point or melting point of 40° C. or greater. The basic silane coupling agent organic carboxylate composition of the present invention can be used directly as an additive (curing agent) for a one-component epoxy resin.

An aliphatic saturated carboxylic acid, aliphatic unsaturated carboxylic acid, aromatic carboxylic acid, or the like can be used as the organic carboxylic acid reacted with the basic silane coupling agent. Desirable organic carboxylic acids from among these include maleic acid, itaconic acid, azelaic acid, phthalic acid, acrylic acid, methacrylic acid, isobutyric acid, octylic acid, formic acid, glyoxylic acid, crotonic acid, acetic acid, propionic acid, benzoic acid, salicylic acid, cyclohexanecarboxylic acid, toluic acid, phenylacetic acid, p-t-butylbenzoic acid, trimellitic acid, trimellitic anhydride, cis-4-cyclohexene dicarboxylic acid, 2-octenyl succinic acid, 2-dodecenyl succinic acid, pyromellitic acid, and the like. The reaction molar ratio of the basic silane coupling agent and organic carboxylic acid should preferably be such that at least one carboxyl group per molecule of the organic carboxylic acid forms a salt with a base. That is, the ratio should preferably be from 1:0.1 to 1:5, and preferably from 1:0.2 to 1:2.

Preferred compounds that have a softening point or melting point of 40° C. or greater and exhibit a good affinity for the basic silane coupling agent or organic carboxylic acid constituting the present invention include those having a softening point or melting point of 40° C. or greater and containing a hydroxyl group, amido group, urea bond, urethane bond, silanol group, amino group, mercapto group, carbonyl group, triazine backbone, or the like. Examples thereof include phenol compounds, a polyvinyl alcohol, an acrylic resin, an EVOH resin, an epoxy resin, an epoxy resin partially or completely modified with acrylic acid or methacrylic acid, a melamine-polyamide resin, a urea resin, a urethane resin, a silicone resin, acid anhydrides, and the like. The role of these compounds is to make the basic silane coupling agent organic carboxylate into a crushable solid and the compounds are required to have miscibility with and good affinity for the basic silane coupling agent or organic carboxylic acid. The merits of the present invention can be sufficiently demonstrated by using the compound having a softening point or melting point of 40° C. or greater. If the softening point or melting point is below 40° C., the resulting product has difficulty hardening, or is difficult to pulverize after hardening. Phenol compounds preferably have at least two phenolic hydroxyl groups per molecule, and examples thereof include bisphenol A, bisphenol F, polyvinyl phenol, phenol novolak resin, cresol novolak resin, bisphenol A novolak resin, bisphenol F novolak resin, aralkyl phenol resins, and the like. In essence, a phenol compound capable of solidifying the composition of the present invention should be selected in an appropriate manner, and such compounds are also believed to be effective in terms of solidification and reactivity in relation to epoxy resins.

The basic silane coupling agent organic carboxylate and the compound exhibiting good affinity for the basic silane coupling agent or organic carboxylic acid and having a softening point or melting point of 40° C. or greater must be mixed in a ratio at which the composition obtained by heating and mixing the organic carboxylate and the compound exhibiting a good affinity for the basic silane coupling agent or organic carboxylic acid and having a softening point or melting point of 40° C. or greater is in a solid form when cooled to room temperature. A basic silane coupling agent organic carboxylate composition that is a solid at room temperature can be obtained by controlling the melting point and mixing ratio of the compound having a softening point or melting point of 40° C. or greater and exhibiting a good affinity for the basic silane coupling agent or organic carboxylic acid to be admixed.

BEST MODE FOR CARRYING OUT THE INVENTION

Examples will be shown hereafter, and the present invention will be described in further detail.

Synthesis of Basic Silane Coupling Agent Organic Carboxylate Composition

Example 1

13.62 g (0.2 mol) of imidazole was melted at 95° C., and 47.27 g (0.2 mol) of (3-glycidoxypropyl)trimethoxysilane was added dropwise thereto over a period of 30 minutes while stirring in an argon atmosphere. Following the addition, the product was further reacted for one hour at a temperature of 95° C., yielding an imidazole group-containing silane coupling agent comprising a mixture of the compounds represented by the chemical formulas (5), (6), and (7) below. 30.4 g (0.1 mol) of the imidazole group-containing silane coupling agent thus obtained and 25.4 g (0.1 mol) of pyromellitic acid were heated and mixed at 120° C., and an imidazole group-containing silane coupling agent pyromellitate was obtained by continuing the reaction for one hour. 20.8 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent pyromellitate/phenol resin composition that was a solid at normal temperatures was obtained by cooling the product to room temperature. The solid product thus obtained was ground with a mortar and classified by a sieve with hole openings of 90 microns to yield pulverized Sample No. 1.

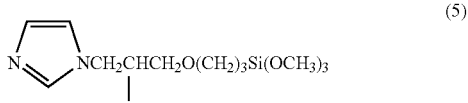

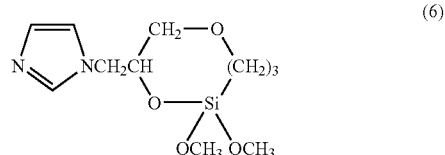

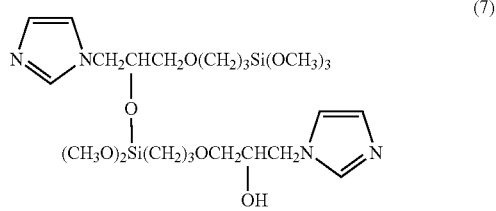

Example 2

30.4 g (0.1 mol) of an imidazole group-containing silane coupling agent obtained in the same manner as in Example 1 and 21.0 g (0.1 mol) of trimellitic acid were heated and mixed at 120° C., and an imidazole group-containing silane coupling agent trimellitate was obtained by continuing the reaction for one hour. 31.2 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent trimellitate/phenol resin composition that was a solid at normal temperatures was obtained by cooling the product to room temperature. The solid product thus obtained was ground with a mortar and classified by a sieve with hole openings of 90 microns to yield pulverized Sample No. 2.

Example 3

30.4 g (0.1 mol) of an imidazole group-containing silane coupling agent obtained in the same manner as in Example 1 and 16.6 g (0.1 mol) of phthalic acid were heated and mixed at 120° C., and an imidazole group-containing silane coupling agent phthalate was obtained by continuing the reaction for one hour. 41.6 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent phthalate-phenol resin composition that was a solid at normal temperatures was obtained by cooling the product to room temperature. The solid product thus obtained was ground with a mortar and classified by a sieve with hole openings of 90 microns to yield pulverized Sample No. 3.

Example 4

13.6 g (0.2 mol) of imidazole and 24.8 g (0.1 mol) of (3-methacryloxypropyl)trimethoxysilane were mixed and reacted at 100° C. for 11 hours. After cooling to room temperature, 100 ml of ethyl acetate was added, and excess imidazole was removed by washing the product three times in 100 ml of pure water. Molecular sieves were added to the product, and the ethyl acetate solution was dried overnight. Subsequently, the ethyl acetate was distilled off in a rotary evaporator, and the imidazole group-containing silane coupling agent expressed by formula (8) below was obtained. 31.6 g (0.1 mol) of the imidazole group-containing silane coupling agent thus obtained and 25.4 g (0.1 mol) of pyromellitic acid were heated and mixed at 120° C., and an imidazole group-containing silane coupling agent pyromellitate was obtained by continuing the reaction for one hour. 20.8 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent pyromellitate/phenol resin composition that was a solid at normal temperatures was obtained by cooling the product to room temperature. The solid product thus obtained was ground with a mortar and classified by a sieve with hole openings of

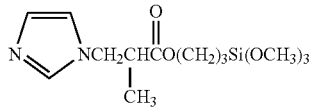

(8)

90 microns to yield pulverized Sample No. 4.

Example 5

31.6 g (0.1 mol) of an imidazole group-containing silane coupling agent obtained in the same manner as in Example 4 and 21.0 g (0.1 mol) of trimellitic acid were heated and mixed at 120° C., and an imidazole group-containing silane coupling agent trimellitate was obtained by continuing the reaction for one hour. 31.2 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent trimellitate/phenol resin composition that was a solid at normal temperatures was obtained by cooling the product to room temperature. The solid product thus obtained was ground with a mortar and classified by a sieve with hole openings of 90 microns to yield pulverized Sample No. 5.

Example 6

31.6 g (0.1 mol) of an imidazole group-containing silane coupling agent obtained in the same manner as in Example 4 and 16.6 g (0.1 mol) of phthalic acid were heated and mixed at 120° C., and an imidazole group-containing silane coupling agent phthalate was obtained by continuing the reaction for one hour. 41.6 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent phthalate/phenol resin composition that was a solid at normal temperatures was obtained by cooling the product to room temperature. The solid product thus obtained was ground with a mortar and classified by a sieve with hole openings of 90 microns to yield pulverized Sample No. 6.

Example 7

31.6 g (0.1 mol) of an imidazole group-containing silane coupling agent obtained in the same manner as in Example 4 and 8.3 g (0.05 mol) of phthalic acid were heated and mixed at 120° C., and an imidazole group-containing silane coupling agent phthalate was obtained by continuing the reaction for one hour. 41.6 g of phenol resin (Phenolite TD-2093 having a softening point of 100° C., mfd. by Dainippon Ink and Chemicals, Inc.) was added to this carboxylate, the product was heated and mixed for one hour at 120° C., and an imidazole group-containing silane coupling agent phthalate/phenol resin composition that was a solid at normal temperatures was obtained by cooling the product to room temperature. The solid product thus obtained was ground with a mortar and classified by a sieve with hole openings of 90 microns to yield pulverized Sample No. 7.

Evaluation of Heat-Softening Properties

The heat-softening properties of the imidazole group-containing silane coupling agent organic carboxylate/phenol compound compositions (Sample Nos. 1-7) obtained in accordance with Examples 1-7 were evaluated using a temperature-controllable hot plate. The results are shown in table 1 below.

TABLE 1

| Evaluation of the Heat-softening Properties of Sample Nos. 1-7 | |
|---|---|
| Sample No. | Temperature of heat-softening (° C.) |
| 1 | Blackening → thermal decomposition at 250° C. |
| 2 | 120° C. |
| 3 | 90° C. |
| 4 | 100° C. |
| 5 | 100° C. |
| 6 | 80° C. |
| 7 | 80° C. |

Evaluation of Adhesion Properties

Examples 8-14

In Examples 8-14, Sample Nos. 1-7 obtained in Examples 1-7 were added as additives for epoxy resin curing, and epoxy resin compositions were produced according to the compositions below.

Epoxy Resin Composition:

Bisphenol A-type epoxy (Epikote 828, mfd. by Japan Epoxy Resins Co., Ltd.): 100 parts by weight Dicyandiamide (AH-154, mfd. by Ajinomoto Co., Inc.): 5 parts by weight 2-Ethyl-4-methylimidazole (2E4MZ, mfd. by Shikoku Chemicals Corp.): 1 part by weight Any of Sample Nos. 1-7:1 part by weight Furthermore, the epoxy resin compositions thus obtained were sandwiched between two sheets of backing material and heat-cured under the conditions described below, yielding bonded materials. SUS 304 with the dimensions described below was used for the backing material, and the material was polished with No. 240 abrasive paper in accordance with JIS K6848 immediately before use, and used after being cleaned with acetone.

Backing material; 100×25×(thickness) 2 (mm)

Curing conditions; 100° C.×1 hour+150° C.×1 hour

Shear adhesive strength was measured for the bonded materials thus obtained, and the effects on adhesion exerted by the additive of the present invention were evaluated. In the evaluation method, the shear adhesive strength of each bonded material was measured at a crosshead speed of 1 mm/min by means of a tensile tester in accordance with JIS K6850. The evaluation results thus obtained are shown in Table 2 below.

Comparative Examples 1 and 2

In Comparative Example 1, an epoxy resin composition and bonded material thereof were produced in the same manner as in Examples 8-14, except that any one of the above-mentioned additives (Sample Nos. 1-7) for the epoxy resin was not added. In Comparative Example 2, an epoxy resin composition and bonded material thereof were also produced in the same manner as in Examples 8-14, except that one part of (3-glycidoxypropyl)trimethoxysilane was added instead of the above-mentioned sample as an additive for the epoxy resin. Adhesion testing was performed in the same manner as in Examples 8-14 for each of the bonded materials thus obtained, and the results are shown in Table 2 below.

TABLE 2

Effects of Adding Sample Nos. 1-7 on Shear Adhesive Strength

|  | Additive | Shear adhesive strength (kN/cm$^2$) |
| --- | --- | --- |
| Example 8 | Sample No. 1 | 1.25 |
| Example 9 | Sample No. 2 | 1.47 |
| Example 10 | Sample No. 3 | 1.38 |
| Example 11 | Sample No. 4 | 1.38 |
| Example 12 | Sample No. 5 | 1.43 |
| Example 13 | Sample No. 6 | 1.42 |
| Example 14 | Sample No. 7 | 1.42 |
| Comparative Example 1 | No additive | 1.02 |
| Comparative Example 2 | (3-Glycidoxypropyl) trimethoxysilane | 1.11 |

Evaluation of Mechanical Characteristics of Cured Material

Examples 15-21

In Examples 15-21, sample Nos. 1-7 obtained in Examples 1-7 were added as additives for epoxy resin curing, and epoxy resin compositions were produced according to the compositions shown below.

Epoxy Resin Composition:

Bisphenol A-type epoxy (Epikote 828, mfd. by Japan Epoxy Resins Co., Ltd.): 100 parts by weight Dicyandiamide (AH-154, mfd. by Ajinomoto Co., Inc.): 5 parts by weight 2-Ethyl-4-methylimidazole (2E4MZ, mfd. by Shikoku Chemicals Corp.): 1 part by weight Any of sample Nos. 1-7:1 part by weight Granular silica filler (RD-8, mfd. by Tatsumori K.K.): 100 parts by weight Subsequently, the epoxy resin compositions were heat-cured under the conditions described below, and epoxy resin cured materials of the dimensions described below were obtained.

Dimensions of cured materials: 80×10×(thickness) 4 (mm)

Curing conditions; 100° C.×1 hour+150° C.×1 hour

The effects exerted on mechanical properties by the additive of the present invention were evaluated for the cured materials thus obtained. In the evaluation method, three-point flexural strength was measured at a crosshead speed of 2 mm/min at the loading point in accordance with JIS K6911. The evaluation results thus obtained are shown in Table 3 below.

Comparative Examples 3 and 4

In Comparative Example 3, an epoxy resin composition and cured material thereof were produced in the same manner as in Examples 15-21, except that any one of the above-mentioned additives (Sample Nos. 1-7) for the epoxy resin was not added. In Comparative Example 4, an epoxy resin composition and cured material thereof were also produced in the same manner as in Examples 15-21, except that one part of (3-glycidoxypropyl)trimethoxysilane was added instead of the above-mentioned sample as an additive for the epoxy resin. Evaluation of mechanical properties was performed in the same manner as in Examples 15-21 for each of the cured materials thus obtained. The results are shown in Table 3 below.

TABLE 3

Effects of Adding Sample Nos. 1-7 on Flexural Strength of Cured Materials

|  | Additive | Flexural strength (N/mm$^2$) |
| --- | --- | --- |
| Example 15 | Sample No. 1 | 102.3 |
| Example 16 | Sample No. 2 | 96.4 |
| Example 17 | Sample No. 3 | 93.0 |
| Example 18 | Sample No. 4 | 96.6 |
| Example 19 | Sample No. 5 | 98.4 |
| Example 20 | Sample No. 6 | 94.0 |
| Example 21 | Sample No. 7 | 96.6 |
| Comparative Example 3 | No additive | 84.1 |
| Comparative Example 4 | (3-Glycidoxypropyl) trimethoxysilane | 90.2 |

Evaluation of Storage Stability and Curing Acceleration

Examples 22-28

In Examples 22-28, Sample Nos. 1-7 produced in Examples 1-7 were added as additives for the epoxy resin, and epoxy resin compositions were produced according to the compositions shown below.

Epoxy Resin Composition:

Bisphenol A-type epoxy (Epikote 828, mfd. by Japan Epoxy Resins Co., Ltd.): 100 parts by weight Dicyandiamide (AH-154, mfd. by Ajinomoto Co., Inc.): 5 parts by weight Any of Sample Nos. 1-7:5 parts by weight The storage stability of the compositions thus obtained was evaluated based on the viscosity change during storage at room temperature. The curing acceleration of each composition was also evaluated by measuring the gelation time thereof on a hot plate set to 150° C. The evaluation results related to storage stability and curing acceleration are shown in Table 4.

Comparative Examples 5 and 6

In Comparative Example 5, an epoxy resin composition was produced in the same manner as in Examples 22-28, except that a product obtained by adding one part of 2-ethyl-4-methylimidazole (2E4MZ, mfd. by Shikoku Chemicals Corp.) was used instead of Sample Nos. 1-7. In Comparative Example 6, an epoxy resin composition was also produced in the same manner as in Examples 22-28, except that any one of the above-mentioned additives (Sample Nos. 1-7) for the epoxy resin was not added. In addition, storage stability and curing acceleration were evaluated in the same manner as in Examples 22-28. The evaluation results are shown in Table 4.

TABLE 4

Effects of Adding Sample Nos. 1-7 on Storage Stability of Epoxy Resin Compositions

| | Additive | Storage stability (viscosity change)* | Curing Acceleration (gelation time) |
|---|---|---|---|
| Example 22 | Sample No. 1 | No change | Not measured |
| Example 23 | Sample No. 2 | No change | Not measured |
| Example 24 | Sample No. 3 | No change | 17 min. and 17 sec. |
| Example 25 | Sample No. 4 | No change | Not measured |
| Example 26 | Sample No. 5 | No change | 12 min. and 18 sec. |
| Example 27 | Sample No. 6 | No change | 9 min. and 30 sec. |
| Example 28 | Sample No. 7 | No change | 7 min. and 9. sec. |
| Comparative Example 5 | 2-ethyl-4-methylimidazole | Hardened due to storage for 10 days | 2 min. and 11 sec. |
| Comparative Example 6 | No additive | No change | 20 min. and 28 sec. |

*"No change" means that any viscosity change was not detected during storage for 10 days.

Application to Sealing Materials

Examples 29 and 30

In Examples 29 and 30, the epoxy resin compositions shown below were obtained using Sample Nos. 2 and 5, produced in the previously described Examples 2 and 5, as additives for the epoxy resin. Subsequently, these epoxy resin compositions were used as sealing materials for copper.

Epoxy Resin Composition:

Epoxy Resin (Biphenyl-type, epoxy equivalent 192): 7.93 parts by weight
Phenol resin (Phenol novolac, hydroxyl group equivalent 106): 4.38 parts by weight Curing accelerator (TPP): 0.25 part by weight Carbon black: 0.20 part by weight Carnauba wax: 0.25 part by weight Filler (MSR-25, spherical silica having a mean grain size of 25 μm, mfd. by Tatsumori K.K.): 87.00 parts by weight Sample No. 2 or 5: 0.4 part by weight (3-glycidoxypropyl)trimethoxysilane: 0.3 part by weight The producing procedure for the sealing material was as follows. The above ingredients were added and mixed in an automated mortar in the following sequence: filler, epoxy resin, phenol resin, TPP, carbon black, carnauba wax, (3-glycidoxypropyl)trimethoxysilane, and Sample No. 2 or 5. The ingredients were then dry-blended directly for 10 minutes using the automated mortar. A heat roller was then heated to 90° C., and the ingredients were heat-kneaded. After the ingredients had blackened, the heat-kneading was still continued for 4 minutes. The ingredients were ultimately crushed for approximately 20 minutes using a stamping mill.

Using the sealing material thus obtained, two sheets of copper material of the dimensions shown below were laminated together, and samples for evaluating adhesion properties were produced. The curing conditions are shown below.

Copper material: C7025 strike-plated with 0.1-μm-thick copper, 50×25×(thickness) 0.15 (mm)

Surface area of adhesion: 25×12.5 mm

Curing conditions: 175° C., 6 hours

Shear strength for these samples was evaluated by the same method as in Examples 8-14. The evaluation results are shown in Table 5 below. Three test pieces were produced for each sample under the same conditions, and the average values for the three pieces are shown in Table 5.

Comparative Example 7

A copper sealing material was produced in the same manner as in Examples 29 and 30, except that Sample No. 2 or 5 as an additive for the epoxy resin was not added. This sealing material was also evaluated for its shear strength in the same manner as in Examples 29 and 30. The evaluation results are shown in Table 5.

TABLE 5

Effects of Adding Sample No. 2 or 5 on Shear Adhesive Strength in Copper Sealing Material

| | Additive | Shear adhesive strength (N/cm$^2$) |
|---|---|---|
| Example 29 | Sample No. 2 | 460 |
| Example 30 | Sample No. 5 | 522 |
| Comparative Example 7 | No additive | 331 |

Production of Basic Silane Coupling Agent Organic Carboxylate Composition and Application Thereof to Sealing Material

Examples 31-48

Basic silane coupling agent organic carboxylate compositions were obtained by using the basic silane coupling agents and organic carboxylic acids shown in Tables 6-1 and 6-2 below together with compounds having a softening point or melting point of 40° C. or greater and exhibiting good affinity for the basic silane coupling agents or organic carboxylates, in the same manner as in Example 7, except that the heating and mixing conditions of the basic silane coupling agents and carboxylic acids as well as the heating and mixing conditions of the resulting basic silane coupling agent organic carboxylates and the compounds having a softening point or melting point of 40° C. or greater and exhibiting good affinity for the basic silane coupling agents or organic carboxylates were 180° C. for 1 hour for Sample Nos. 14, 22, and 23, and 120° C. for the other samples. The products were crushed in a ball mill and classified by a sieve with hole openings of 90 microns to yield pulverized Sample Nos. 8-25.

TABLE 6

| Sample No. | |
|---|---|
| 8 | (3-aminopropyl) trimethoxysilane: 0.1 mol<br>Trimellitic acid: 0.1 mol<br>Phenol resin (TD-2093) (softening point 100° C.): 41.6 g |
| 9 | N-methylaminopropyltrimethoxysilane: 0.1 mol<br>Trimellitic acid: 0.1 mol<br>Phenol resin (TD-2093) (softening point 100° C.): 41.6 g |
| 10 | Dimethylaminosilane synthesized in Reference Example 1 of Japanese Patent Application Publication No. 9-296135: 0.1 mol<br>Trimellitic acid: 0.1 mol<br>Phenol resin (TD-2093) (softening point 100° C.): 41.6 g |
| 11 | Benzotriazole group-containing silane coupling agent synthesized in Example 1 of Japanese Patent Application Publication No. 6-279463: 0.1 mol<br>Trimellitic acid: 0.1 mol<br>Phenol resin (TD-2093) (softening point 100° C.): 41.6 g |
| 12 | Benzimidazole group-containing silane coupling agent synthesized in Example 1 of Japanese Patent Application Publication No. 6-279458: 0.1 mol<br>Trimellitic acid: 0.1 mol<br>Phenol resin (TD-2093) (softening point 100° C.): 41.6 g |
| 13 | Pyridine ring-containing silane coupling agent synthesized in Example 1 of Japanese Patent Application Publication No. 9-295991: 0.1 mol<br>Trimellitic acid: 0.1 mol<br>Phenol resin (TD-2093) (softening point 100° C.): 41.6 g |
| 14 | Imidazole group-containing silane coupling agent obtained in the same manner as in Example 1: 0.1 mol<br>Trimellitic acid: 0.1 mol<br>Polyvinyl alcohol (melting point 180° C.): 30 g |
| 15 | Imidazole group-containing silane coupling agent obtained in the same manner as in Example 1: 0.1 mol<br>Trimellitic acid: 0.1 mol<br>Acrylic polymer (polymer resulting from polymerization of 2-hydroxyethyl methacrylate) (softening point 55° C.): 30 g |
| 16 | Imidazole group-containing silane coupling agent obtained in the same manner as in Example 1: 0.1 mol<br>Trimellitic acid: 0.1 mol<br>Bisphenol A-type epoxy resin (softening point 64° C.): 30 g |
| 17 | Imidazole group-containing silane coupling agent obtained in the same manner as in Example 1: 0.1 mol<br>Trimellitic acid: 0.1 mol<br>Bisphenol A-type epoxy resin modified with methacrylic acid (softening point 55° C.): 30 g |
| 18 | Imidazole group-containing silane coupling agent obtained in the same manner as in Example 1: 0.1 mol<br>Trimellitic acid: 0.1 mol<br>Melamine resin (partially methylated polymer obtained following methylolation of melamine with formaldehyde) (softening point 50° C. or greater): 30 g |
| 19 | Imidazole group-containing silane coupling agent obtained in the same manner as in Example 1: 0.1 mol<br>Trimellitic acid: 0.1 mol<br>Urea resin (resin obtained by adjusting 1 mol of urea and 2 mol of formaldehyde to pH 7 with a basic catalyst, reacting the components at 50° C., dissolving hexamethylenetetramine to 3%, adding 25% α-cellulose, mixing the product in a kneader, and drying) (softening point 50° C. or greater): 30 g |
| 20 | Imidazole group-containing silane coupling agent obtained in the same manner as in Example 1: 0.1 mol<br>Trimellitic acid: 0.1 mol<br>Polyurethane (type in which a small quantity of unreacted isocyanate remains) (softening point 50° C. or greater): 30 g |
| 21 | Imidazole group-containing silane coupling agent obtained in the same manner as in Example 1: 0.1 mol<br>Trimellitic acid: 0.1 mol<br>Silicone resin (polycondensate in which methyltrimethoxysilane and aminopropyl trimethoxysilane were subjected to hydrolysis and condensation and polymerization) (softening point 50° C. or greater): 30 g |
| 22 | Imidazole group-containing silane coupling agent obtained in the same manner as in Example 1: 0.1 mol<br>Trimellitic acid: 0.1 mol<br>EVOH resin (ethylene-vinyl alcohol copolymer, ethylene copolymerization ratio 38%, melting point 175° C.): 30 g |
| 23 | Imidazole group-containing silane coupling agent obtained in the same manner as in Example 1: 0.1 mol<br>Trimellitic acid: 0.1 mol<br>Polyamide (nylon 10, melting point 177° C.): 30 g |
| 24 | (3-aminopropyl) trimethoxysilane: 0.1 mol<br>Trimellitic acid: 0.033 mol<br>Phenol resin (TD-2093) (softening point 100° C.): 41.6 g |
| 25 | (3-aminopropyl) triethoxysilane: 0.1 mol<br>Trimellitic acid: 0.1 mol<br>Phenol resin (TD-2093) (softening point 100° C.): 41.6 g |

Using the samples thus obtained, sealing materials were produced and shear adhesive strength was evaluated in the same manner as in Example 29. The results are shown in Table 7 below.

TABLE 7

| | Additive | Shear adhesive strength (N/cm$^2$) |
|---|---|---|
| Example 31 | Sample No. 8 | 408 |
| Example 32 | Sample No. 9 | 396 |
| Example 33 | Sample No. 10 | 461 |
| Example 34 | Sample No. 11 | 385 |
| Example 35 | Sample No. 12 | 440 |
| Example 36 | Sample No. 13 | 426 |
| Example 37 | Sample No. 14 | 405 |
| Example 38 | Sample No. 15 | 361 |
| Example 39 | Sample No. 16 | 489 |
| Example 40 | Sample No. 17 | 368 |
| Example 41 | Sample No. 18 | 433 |
| Example 42 | Sample No. 19 | 393 |
| Example 43 | Sample No. 20 | 355 |
| Example 44 | Sample No. 21 | 360 |
| Example 45 | Sample No. 22 | 358 |
| Example 46 | Sample No. 23 | 395 |
| Example 47 | Sample No. 24 | 405 |
| Example 48 | Sample No. 25 | 410 |

INDUSTRIAL APPLICABILITY

The basic silane coupling agent organic carboxylate composition of the present invention is a solid at room temperature and can also function as a silane coupling agent. Applications thereof include not only functioning as an exceptional adhesion enhancer when added to a one-component epoxy resin composition, but also serving as an additive which imparts a long working life due to being a solid at room temperature and having an organic carboxylate structure. Furthermore, the composition of the present invention is extremely useful as an additive for an epoxy resin that has a high storage stability. The composition of the present invention can also be pulverized and used in powdered coating materials because it has a relatively high heat-softening temperature and can be pulverized. In addition, the adhesiveness, mechanical properties, and storage stability satisfy the characteristics required for application to epoxy resin compositions in a wide range of possible applications, including adhesives, paints, laminates, moldings, printed wiring boards, copper-clad laminates, resin-coated copper foil, semiconductor chip coating materials, semiconductor chip mounting materials, photoresists, solder resists, dry film resists, and the like.

What is claimed is:

1. A method for producing a pulverized additive for a resin, comprising the steps of:
reacting a basic silane coupling agent and an organic carboxylic acid to produce an organic carboxylate of a basic silane coupling agent;
heating and mixing the organic carboxylate of the basic silane coupling agent and a compound exhibiting a good affinity for the basic silane coupling agent or organic carboxylic acid and having a softening point or melting point of at least 40° C. to obtain a basic silane coupling agent organic carboxylate composition; and
pulverizing the basic silane coupling agent organic carboxylate composition.

2. The method according to claim 1, wherein the basic silane coupling agent is comprised of at least one member selected from the group consisting of the compounds expressed by the general formulas (1) through (4), or at least one of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents,

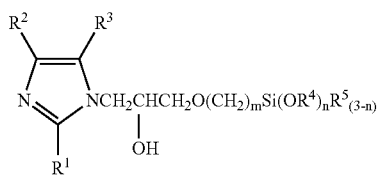

(1)

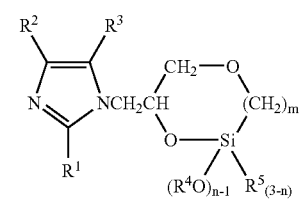

(2)

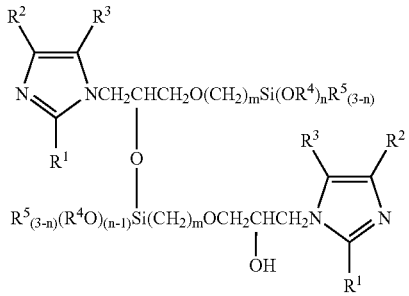

(3)

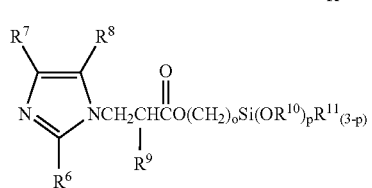

(4)

wherein in the general formulas (1) through (4),
$R^1$ to $R^3$ each represent hydrogen, a vinyl group, or an alkyl group having 1 to 20 carbon atoms wherein the $R^2$ and $R^3$ may form an aromatic ring;
$R^4$ and $R^5$ each represent an alkyl group having 1-5 carbon atoms;
$R^6$ to $R^8$ each represent hydrogen, an alkyl group having 1 to 20 carbon atoms, a vinyl group, a phenyl group, or a benzyl group wherein $R^7$ and $R^8$ may bond and form an aromatic ring;
$R^9$ represents hydrogen or an alkyl group having 1 to 3 carbon atoms;
$R^{10}$ and $R^{11}$ each represent an alkyl group having 1 to 5 carbon atoms; and
m, n, o, and p are integers of 1 to 10, 1 to 3, 1 to 10, and 1 to 3, respectively.

* * * * *